(12) United States Patent
Huang et al.

(10) Patent No.: US 10,048,226 B2
(45) Date of Patent: Aug. 14, 2018

(54) IMAGING METHOD AND APPARATUS BASED ON MAGNETIC FLUX LEAKAGE TESTING

(71) Applicants: Tsinghua University, Beijing (CN); Shengli Oilfield Branch Company of China Petroleum Chemical Co., Ltd., Dongying, Shandong Province (CN); Drilling Technology Research Institute of Sinopec Shengli Petroleum Engineering Co., Ltd., Dongying, Shandong Province (CN)

(72) Inventors: Songling Huang, Beijing (CN); Wei Zhao, Beijing (CN); Shen Wang, Beijing (CN); Huanquan Sun, Dongying (CN); Laiju Han, Dongying (CN); Shihua Zhang, Dongying (CN); Yongtai Sun, Dongying (CN)

(73) Assignees: Tsinghua University, Beijing (CN); Shengli Oilfield Branch Company of China Petroleum Chemical Co., Ltd., Dongying, Shandong Province (CN); Drilling Technology Research Institute of Sinopec Shengli Petroleum Engineering Co., Ltd., Dongying, Shandong Province (CN)

( * ) Notice: Subject to any disclaimer, the term of this patent is extended or adjusted under 35 U.S.C. 154(b) by 245 days.

(21) Appl. No.: 14/961,367

(22) Filed: Dec. 7, 2015

(65) Prior Publication Data
US 2016/0161448 A1 Jun. 9, 2016

(30) Foreign Application Priority Data
Dec. 8, 2014 (CN) .......................... 2014 1 0743400

(51) Int. Cl.
*G06K 9/00* (2006.01)
*G01N 27/82* (2006.01)
*G01N 17/04* (2006.01)

(52) U.S. Cl.
CPC ............. *G01N 27/82* (2013.01); *G01N 17/04* (2013.01)

(58) Field of Classification Search
CPC ........ G01N 27/82; G01N 27/83; G01N 21/88; G01N 17/04; G06T 7/0004; G06T 7/001; G06T 2207/30148; G06T 2207/30164
See application file for complete search history.

(56) References Cited

U.S. PATENT DOCUMENTS

| | | | | | |
|---|---|---|---|---|---|
| 4,063,157 A | * | 12/1977 | Lorenzi | .................. | G01N 27/82 324/213 |
| 4,096,437 A | * | 6/1978 | Kitzinger | ............... | G01N 27/82 324/227 |

(Continued)

*Primary Examiner* — Amir Alavi
(74) *Attorney, Agent, or Firm* — Kile Park Reed & Houtteman PLLC

(57) ABSTRACT

An imaging method and an imaging apparatus based on a magnetic flux leakage testing. The imaging method includes: selecting an imaging region having a corrosion defect on a pipeline to be tested; dividing the imaging region into a plurality of grid areas; scanning by a three-dimensional sensor array the pipeline to be tested so as to obtain magnetic flux leakage testing data; creating a three-dimensional orthogonal coordinate system in the imaging region, defining a first two-dimensional matrix of defect images according to the plurality of grid areas based on the three-dimensional orthogonal coordinate system, and creating a second two-dimensional matrix of magnetic flux leakage signals according to the magnetic flux leakage testing data based on the three-dimensional orthogonal coordinate system; and mapping the second two-dimensional matrix to the (Continued)

first two-dimensional matrix using a pre-trained wavelet neural network so as to image the corrosion defect.

15 Claims, 3 Drawing Sheets

(56) References Cited

U.S. PATENT DOCUMENTS

| | | | | | |
|---|---|---|---|---|---|
| 4,492,115 | A | * | 1/1985 | Kahil | G01N 27/82 324/226 |
| 4,659,991 | A | * | 4/1987 | Weischedel | G01N 27/82 324/241 |
| 6,344,741 | B1 | * | 2/2002 | Giguere | G01N 17/006 324/225 |
| 2005/0267686 | A1 | * | 12/2005 | Ward | E21B 43/127 702/6 |
| 2006/0076951 | A1 | * | 4/2006 | Nestleroth | G01N 27/82 324/220 |
| 2015/0091555 | A1 | * | 4/2015 | Huang | G01N 27/82 324/209 |
| 2016/0161448 | A1 | * | 6/2016 | Huang | G01N 27/82 324/220 |
| 2016/0178580 | A1 | * | 6/2016 | Huang | G01N 27/83 702/190 |

* cited by examiner

IMAGING METHOD AND APPARATUS BASED ON MAGNETIC FLUX LEAKAGE TESTING

CROSS-REFERENCE TO RELATED APPLICATIONS

This application claims priority to and benefits of Chinese Patent Application No. 201410743400.1, filed with the State Intellectual Property Office of P. R. China on Dec. 8, 2014, the entire contents of which are incorporated herein by reference.

TECHNICAL FIELD

The present disclosure generally relates to a nondestructive testing technology, and more particularly, to an imaging method and an imaging apparatus for a magnetic flux leakage testing.

BACKGROUND

A magnetic flux leakage testing is a common nondestructive testing method, which is widely used in a quality testing and a safety monitoring of ferromagnetic material. In recent years, with a continuous improvement and progress of a defect quantification technology, people want to convert a corrosion defect distribution of a pipeline into a form of graphics and images which may be identified directly by naked eyes and further to present the form of graphics and images on a screen in order to achieve the defect visualization.

However, in the related art, defect parameters in three directions may be quantized, but an image corresponding to the defect cannot be generated; or there is a technology to determine which layer of a steel plate the defect is locate, but the technology does not mention the image method of the defect.

SUMMARY

A first aspect of the present disclosure is to provide an imaging method based on a magnetic flux leakage testing. The imaging method includes: selecting an imaging region having a corrosion defect on a pipeline to be tested; dividing the imaging region into a plurality of grid areas; scanning by a three-dimensional sensor array the pipeline to be tested so as to obtain magnetic flux leakage testing data; creating a three-dimensional orthogonal coordinate system in the imaging region, defining a first two-dimensional matrix of defect images according to the plurality of grid areas based on the three-dimensional orthogonal coordinate system, and creating a second two-dimensional matrix of magnetic flux leakage signals according to the magnetic flux leakage testing data based on the three-dimensional orthogonal coordinate system; and mapping the second two-dimensional matrix to the first two-dimensional matrix using a pre-trained wavelet neural network so as to image the corrosion defect.

In some embodiments, each grid area represents a pixel of the defect image and each element in the first two-dimensional matrix represents a defect depth at a pixel.

In some embodiments, before scanning by a three-dimensional sensor array the pipeline to be tested, the imaging method further includes saturation magnetizing the pipeline to be tested by a direct current magnetic field.

In some embodiments, scanning by an three-dimensional sensor array the pipeline to be tested so as to obtain magnetic flux leakage testing data includes: obtaining original magnetic flux leakage data by scanning the pipeline to be tested; calculating an average value of the original magnetic flux leakage data; obtaining an anomaly threshold according to the average value; and filtering the original magnetic flux leakage data according to the anomaly threshold to obtain the magnetic flux leakage testing data.

In some embodiments, the first two-dimensional matrix is denoted by $$f(x,y) = \begin{bmatrix} f(0,0) & f(0,1) & \ldots & f(0,N-1) \\ f(1,0) & f(1,1) & \ldots & f(1,N-1) \\ \vdots & \vdots & & \vdots \\ f(M-1,0) & f(M-1,1) & \ldots & f(M-1,N-1) \end{bmatrix}$$

where x represents a coordinate corresponding to a defect length of the corrosion defect in the three-dimensional orthogonal coordinate system, y represents a coordinate corresponding to a defect width of the corrosion defect in the three-dimensional orthogonal coordinate system, M represents a number of pixels collected in a length direction of the corrosion defect, N represents a number of pixels collected in a width direction of the corrosion defect, f(x,y) represents a defect depth of the corrosion defect; f(0,0) represents a defect depth at a pixel representing a first pixel in the length direction and a first pixel in the width direction; f(0,1) represents a defect depth at a pixel representing a first pixel in the length direction and a second pixel in the width direction; f(M−1,N−1) represents a defect depth at a pixel representing a $M^{th}$ pixel in the length direction and a $N^{th}$ pixel in the width direction.

In some embodiments, the magnetic flux leakage testing data comprises: magnetic flux leakage testing data in an axial direction of the pipeline to be tested, magnetic flux leakage testing data in a radial direction of the pipeline to be tested and magnetic flux leakage testing data in a circumferential direction of the pipeline to be tested; and the second two-dimensional matrix comprises: a third two-dimensional matrix of magnetic flux leakage signals in the axial direction, a fourth two-dimensional matrix of magnetic flux leakage signals in the radial direction and a fifth two-dimensional matrix of magnetic flux leakage signals in the circumferential direction.

In some embodiments, the third two-dimensional matrix is denoted by $$B_a = \begin{bmatrix} B_{a11} & B_{a12} & \ldots & B_{a1K} \\ B_{a21} & B_{a22} & \ldots & B_{a2K} \\ \vdots & \vdots & \vdots & \vdots \\ B_{aJ1} & B_{aJ2} & \ldots & B_{aJK} \end{bmatrix};$$

the fourth two-dimensional matrix is denoted by $$B_r = \begin{bmatrix} B_{r11} & B_{r12} & \ldots & B_{r1K} \\ B_{r21} & B_{r22} & \ldots & B_{r2K} \\ \vdots & \vdots & \vdots & \vdots \\ B_{rJ1} & B_{rJ2} & \ldots & B_{rJK} \end{bmatrix};$$

the fifth two-dimensional matrix is denoted by $$B_c = \begin{bmatrix} B_{c11} & B_{c12} & \ldots & B_{c1K} \\ B_{c21} & B_{c22} & \ldots & B_{c2K} \\ \vdots & \vdots & \vdots & \vdots \\ B_{cJ1} & B_{cJ2} & \ldots & B_{cJK} \end{bmatrix},$$

where J represents a number of measuring points in a axial direction of the pipeline to be tested, K represents a number of measuring points in a circumferential direction of the pipeline to be tested, $B_{a11}$ represents a magnetic flux leakage signal in the axial direction at a measuring point representing a first measuring point in the axial direction and a first measuring point in the circumferential direction; $B_{aJK}$ represents a magnetic flux leakage signal in the axial direction at a measuring point representing a $J^{th}$ measuring point in the axial direction and a $K^{th}$ measuring point in the circumferential direction; $B_{r11}$ represents a magnetic flux leakage signal in the radial direction at a measuring point representing a first measuring point in the axial direction and a first measuring point in the circumferential direction; $B_{rJK}$ represents a magnetic flux leakage signal in the radial direction at a measuring point representing a $J^{th}$ measuring point in the axial direction and a $K^{th}$ measuring point in the circumferential direction; $B_{c11}$ represents a magnetic flux leakage signal in the circumferential direction at a measuring point representing a first measuring point in the axial direction and a first measuring point in the circumferential direction; $B_{cJK}$ represents a magnetic flux leakage signal in the circumferential direction at a measuring point representing a $J^{th}$ measuring point in the axial direction and a $K^{th}$ measuring point in the circumferential direction.

With the imaging method based on a magnetic flux leakage testing according to embodiments of the present disclosure, the imaging region of the defect is discretized, i.e. the imaging region is divided into the plurality of grid areas, in which each grid area represents a pixel, then the pipeline to be tested is scanned by the three-dimensional sensor array to obtain the magnetic flux leakage testing data, and then the three-dimensional orthogonal coordinate system is created in the imaging region while the first two-dimensional matrix of defect images and the second two-dimensional matrix of magnetic flux leakage signals are defined, in which the elements of the first two-dimensional matrix correspond respectively to the elements of the second two-dimensional matrix, and finally the second two-dimensional matrix is mapped into the first two-dimensional matrix using the pre-trained wavelet neural network, such that a reconstruction of a three-dimensional contour of the defect is realized. Therefore, the method obtains the data by the three-dimensional sensor array and the signal characteristics are from many sources, thus overcoming a disadvantage of only using characteristics of magnetic flux leakage signals in the axial direction to estimate in the conventional technology, meanwhile, the method takes advantages of a parallel computing, a fast speed and a accurate mapping in the training of the wavelet neural network, thus realizing a three-dimensional imaging and visualization of the defect and having a broad application prospect.

A second aspect of the present disclosure is to provide an imaging apparatus based on a magnetic flux leakage testing. The imaging apparatus includes: a processor; a memory for storing instructions executable by the processor; wherein the processor is configured to: select an imaging region having a corrosion defect on a pipeline to be tested; divide the imaging region into a plurality of grid areas; control a three-dimensional sensor array to scan the pipeline to be tested to obtain magnetic flux leakage testing data; create a three-dimensional orthogonal coordinate system in the imaging region, define a first two-dimensional matrix of defect images according to the plurality of grid areas based on the three-dimensional orthogonal coordinate system, and create a second two-dimensional matrix of magnetic flux leakage signals according to the magnetic flux leakage testing data based on the three-dimensional orthogonal coordinate system; and map the second two-dimensional matrix to the first two-dimensional matrix using a pre-trained wavelet neural network so as to image the corrosion defect.

In some embodiments, each grid area represents a pixel of the defect image and each element in the first two-dimensional matrix represents a defect depth at a pixel.

In some embodiments, the processor further configured to saturation magnetize on the pipeline to be tested by a direct current magnetic field before controlling a three-dimensional sensor array to scan the pipeline to be tested.

In some embodiments, the processor is configured to control a three-dimensional sensor array to scan the pipeline to be tested so as to obtain magnetic flux leakage testing data by steps of: obtaining original magnetic flux leakage data by scanning the pipeline to be tested; calculating an average value of the original magnetic flux leakage data; obtaining an anomaly threshold according to the average value; filtering the original magnetic flux leakage data according to the anomaly threshold to obtain the magnetic flux leakage testing data.

In some embodiments, the first two-dimensional matrix is denoted by $$f(x, y) = \begin{bmatrix} f(0, 0) & f(0, 1) & \ldots & f(0, N-1) \\ f(1, 0) & f(1, 1) & \ldots & f(1, N-1) \\ \vdots & \vdots & & \vdots \\ f(M-1, 0) & f(M-1, 1) & \ldots & f(M-1, N-1) \end{bmatrix}$$

where x represents a coordinate corresponding to a defect length of the corrosion defect in the three-dimensional orthogonal coordinate system, y represents a coordinate corresponding to a defect width of the corrosion defect in the three-dimensional orthogonal coordinate system, M represents a number of pixels collected in a length direction of the corrosion defect, N represents a number of pixels collected in a width direction of the corrosion defect, f(x,y) represents a defect depth of the corrosion defect; f(0,0) represents a defect depth at a pixel representing a first pixel in the length direction and a first pixel in the width direction; f(0,1) represents a defect depth at a pixel representing a first pixel in the length direction and a second pixel in the width direction; f(M−1,N−1) represents a defect depth at a pixel representing a $M^{th}$ pixel in the length direction and a $N^{th}$ pixel in the width direction.

In some embodiments, the tested magnetic flux leakage data includes tested magnetic flux leakage data in an axial direction, tested magnetic flux leakage data in a radial direction and tested magnetic flux leakage data in a circumferential direction, the two-dimensional matrix of magnetic flux leakage signals includes a two-dimensional matrix of magnetic flux leakage signals in the axial direction, a two-dimensional matrix of magnetic flux leakage signals in the radial direction and a two-dimensional matrix of magnetic flux leakage signals in the circumferential direction.

In some embodiments, the magnetic flux leakage testing data comprises: magnetic flux leakage testing data in an axial direction of the pipeline to be tested, magnetic flux leakage testing data in a radial direction of the pipeline to be tested and magnetic flux leakage testing data in a circumferential direction of the pipeline to be tested; and the second two-dimensional matrix comprises: a third two-dimensional matrix of magnetic flux leakage signals in the axial direction, a fourth two-dimensional matrix of magnetic flux leakage signals in the radial direction and a fifth two-dimensional matrix of magnetic flux leakage signals in the circumferential direction.

In some embodiments, the third two-dimensional matrix is denoted by $$B_a = \begin{bmatrix} B_{a11} & B_{a12} & \ldots & B_{a1K} \\ B_{a21} & B_{a22} & \ldots & B_{a2K} \\ \vdots & \vdots & \vdots & \vdots \\ B_{aJ1} & B_{aJ2} & \ldots & B_{aJK} \end{bmatrix};$$

the fourth two-dimensional matrix is denoted by $$B_r = \begin{bmatrix} B_{r11} & B_{r12} & \ldots & B_{r1K} \\ B_{r21} & B_{r22} & \ldots & B_{r2K} \\ \vdots & \vdots & \vdots & \vdots \\ B_{rJ1} & B_{rJ2} & \ldots & B_{rJK} \end{bmatrix};$$

the fifth two-dimensional matrix is denoted by $$B_c = \begin{bmatrix} B_{c11} & B_{c12} & \ldots & B_{c1K} \\ B_{c21} & B_{c22} & \ldots & B_{c2K} \\ \vdots & \vdots & \vdots & \vdots \\ B_{cJ1} & B_{cJ2} & \ldots & B_{cJK} \end{bmatrix},$$

where J represents a number of measuring points in a axial direction of the pipeline to be tested, K represents a number of measuring points in a circumferential direction of the pipeline to be tested, $B_{a11}$ represents a magnetic flux leakage signal in the axial direction at a measuring point representing a first measuring point in the axial direction and a first measuring point in the circumferential direction; $B_{aJK}$ represents a magnetic flux leakage signal in the axial direction at a measuring point representing a $J^{th}$ measuring point in the axial direction and a $K^{th}$ measuring point in the circumferential direction; $B_{r11}$ represents a magnetic flux leakage signal in the radial direction at a measuring point representing a first measuring point in the axial direction and a first measuring point in the circumferential direction; $B_{rJK}$ represents a magnetic flux leakage signal in the radial direction at a measuring point representing a $J^{th}$ measuring point in the axial direction and a $K^{th}$ measuring point in the circumferential direction; $B_{c11}$ represents a magnetic flux leakage signal in the circumferential direction at a measuring point representing a first measuring point in the axial direction and a first measuring point in the circumferential direction; $B_{cJK}$ represents a magnetic flux leakage signal in the circumferential direction at a measuring point representing a $J^{th}$ measuring point in the axial direction and a $K^{th}$ measuring point in the circumferential direction.

With the imaging apparatus based on a magnetic flux leakage testing according to embodiments of the present disclosure, the imaging region of the defect is discretized, i.e. the imaging region is divided into the plurality of grid areas, in which each grid area represents a pixel, then the pipeline to be tested is scanned by the three-dimensional sensor array to obtain the magnetic flux leakage testing data, and then the three-dimensional orthogonal coordinate system is created in the imaging region while the first two-dimensional matrix of defect images and the second two-dimensional matrix of magnetic flux leakage signals are defined, in which the elements of the first two-dimensional matrix correspond respectively to the elements of the second two-dimensional matrix, and finally the second two-dimensional matrix is mapped into the first two-dimensional matrix using the pre-trained wavelet neural network, such that a reconstruction of a three-dimensional contour of the defect is realized. Therefore, the method obtains the data by the three-dimensional sensor array and the signal characteristics are from many sources, thus overcoming a disadvantage of only using characteristics of magnetic flux leakage signals in the axial direction to estimate in the conventional technology, meanwhile, the method takes advantages of a parallel computing, a fast speed and a accurate mapping in the training of the wavelet neural network, thus realizing a three-dimensional imaging and visualization of the defect and having a broad application prospect.

A third aspect of the present disclosure is to provide a computer readable storage medium having stored therein a computer program, when executed by a computer, to perform the imaging method based on a magnetic flux leakage testing according to embodiments of the first aspect of the present disclosure, when running on a computer.

Additional aspects and advantages of embodiments of present disclosure will be given in part in the following descriptions, become apparent in part from the following descriptions, or be learned from the practice of the embodiments of the present disclosure.

BRIEF DESCRIPTION OF THE DRAWINGS

These and other aspects and advantages of embodiments of the present disclosure will become apparent and more readily appreciated from the following descriptions made with reference to the accompanying drawings, in which.

DETAILED DESCRIPTION

Figure 1:
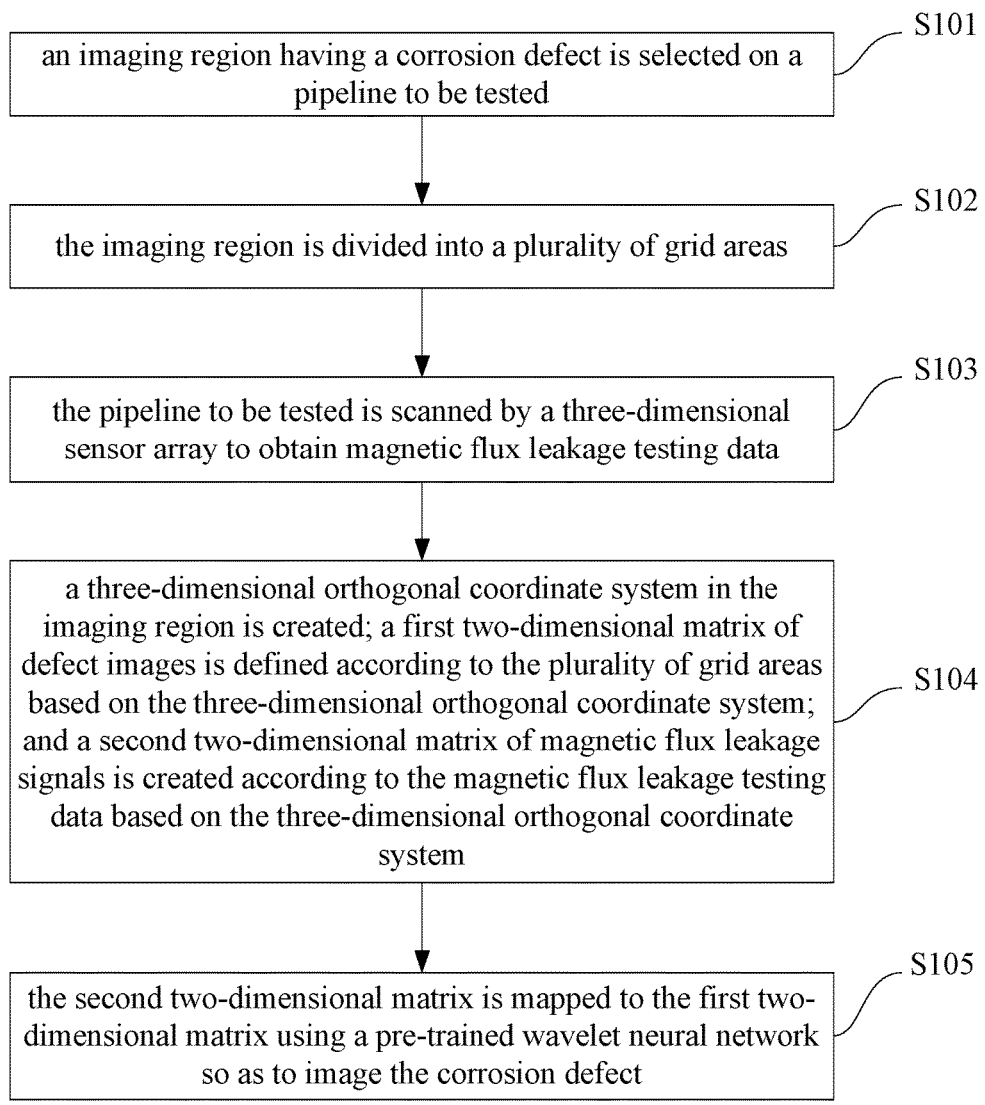
FIG. 1 is a flow chart of an imaging method based on a magnetic flux leakage testing according to an embodiment of the present disclosure.

Reference will be made in detail to embodiments of the present disclosure. Embodiments of the present disclosure will be shown in drawings, in which the same or similar elements and the elements having same or similar functions are denoted by like reference numerals throughout the descriptions. The embodiments described herein according to drawings are explanatory and illustrative, not construed to limit the present disclosure.

In the following, an imaging method and an imaging apparatus based on a magnetic flux leakage testing according to embodiments of the present disclosure will be described with reference to accompanying drawings.

Figure 2:
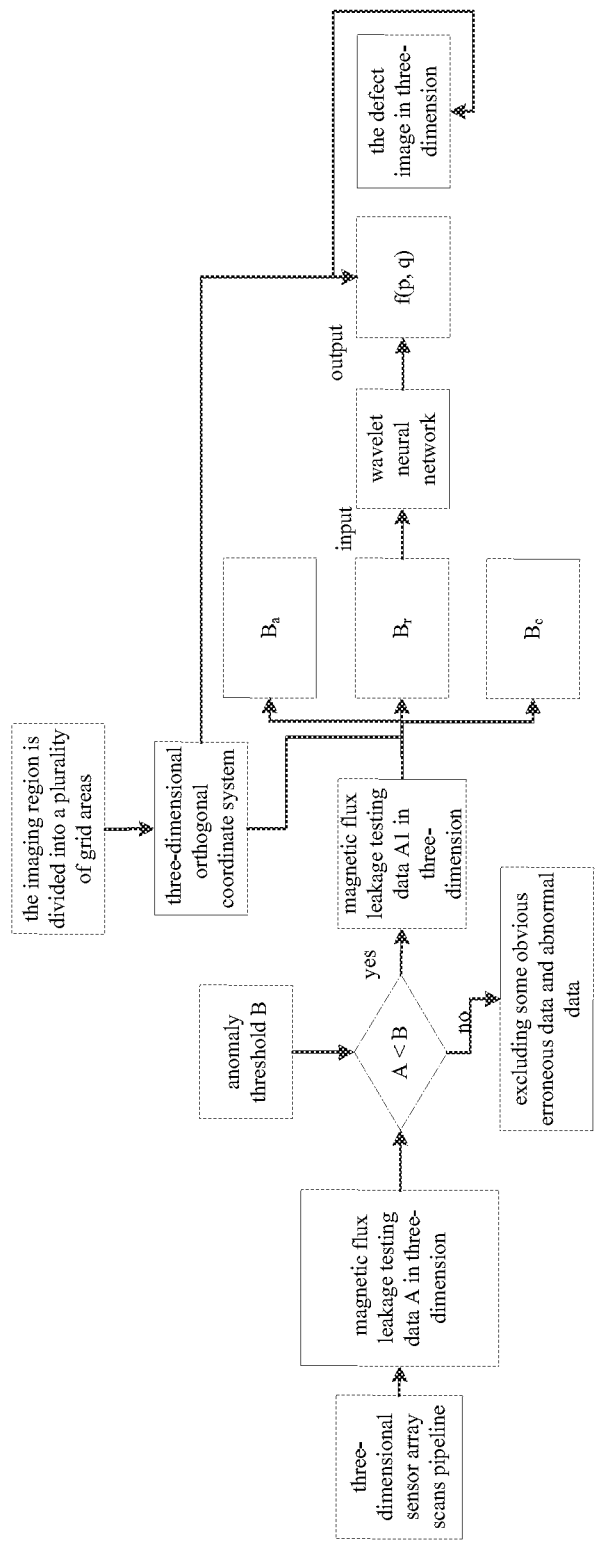
FIG. 2 is a flow chart of an imaging method based on a magnetic flux leakage testing according to another embodiment of the present disclosure.

FIG. 1 is a flow chart of an imaging method based on a magnetic flux leakage testing according to an embodiment of the present disclosure and FIG. 2 is a flow chart of an imaging method based on a magnetic flux leakage testing according to another embodiment of the present disclosure. Referring to FIG. 1 and FIG. 2, the imaging method includes following steps.

In step S101, an imaging region having a corrosion defect is selected on a pipeline to be tested.

In other words, the pipeline to be tested may be provided, and then the imaging region on the pipeline to be tested is selected, in which the imaging region includes the corrosion defect.

In step S102, the imaging region is divided into a plurality of grid areas.

In some exemplary embodiments, for example, the pipeline to be tested having a thickness T is provided, and then a region having an area A×B is selected from the pipeline as the imaging region. A standard artificial corrosion defect having a length 2.5T, a width 1.5T and a depth 0.1~1T is formed in the imaging region. And then the imaging region is divided into M×N grid areas (i.e. M×N pixels), i.e. a defect length is discretized into M points and a defect width is discretized into N points, such that a sampling interval in a length direction of the imaging region is equal to S1=A/M, a sampling interval in a width direction of the imaging region is equal to S2=B/N and an area occupied by each pixel is equal to S1×S2. Boundaries of the corrosion defect are transited naturally in arc. The thickness T is about 7.0~36.0 mm.

It should be noted that, a size of the pipeline, a size of the imaging region, a size of the grid area, and a dividing method of the grid areas are illustrative, and it would be appreciated by those skilled in the art that the above-described cannot be construed to limit the present disclosure.

In step S103, the pipeline to be tested is scanned by a three-dimensional sensor array to obtain magnetic flux leakage testing data. The three-dimensional sensor array includes a plurality of sensors disposed in a circumferential direction of the pipeline to be tested. The three-dimensional sensor array moves in the pipeline to be tested along a axial direction of the pipeline to be tested to scan the pipeline to be tested.

In some embodiments, before the pipeline to be tested is scanned by the three-dimensional sensor array, the method further includes a step of: saturation magnetizing the pipeline to be tested by a direct current magnetic field.

Further, step S103 includes following steps.

In step 1, original magnetic flux leakage data is obtained by scanning the pipeline to be tested.

In some exemplary embodiments, in other words, a saturation magnetization is performed on the pipeline to be tested by the direct current magnetic field, and then the three-dimensional sensor array samples data at equal intervals in the pipeline to be tested at a certain operating speed to obtain the original magnetic flux leakage data of the pipeline to be tested, in which the original magnetic flux leakage data includes original magnetic flux leakage data in an axial direction, original magnetic flux leakage data in a radial direction and original magnetic flux leakage data in a circumferential direction. During the scanning, a liftoff value of the sensor is required to be maintained in 1.0~5.0 mm. The sensor is a Hall sensor, and the liftoff value of the sensor is a distance from the Hall sensor to a surface of an inner wall of the pipeline. The sampling interval d is 0.1~8.0 mm, and the operating speed V is 0.1~5.0 m/s.

In step 2, an average value of the original magnetic flux leakage data is calculated.

In some exemplary embodiments, in other words, the original magnetic flux leakage data obtained in step 1 is calculated to obtain the average value.

In step 3, an anomaly threshold is obtained according to the average value.

In some exemplary embodiments, the anomaly threshold is equal to 1.2~1.5 times of the average value.

In step 4, the original magnetic flux leakage data is faltered according to the anomaly threshold to obtain the magnetic flux leakage testing data. In other words, the data in the original magnetic flux leakage data which is larger than the anomaly threshold obtained in step 3 is deleted, thus excluding some obvious erroneous data and abnormal data.

It should be noted that, the above-described values are illustrative, and the sampling interval, the operating speed, the liftoff value of the sensor, the anomaly threshold and so on may be different in different applications. It would be appreciated by those skilled in the art that the above-described values cannot be construed to limit the present disclosure.

In step S104, a three-dimensional orthogonal coordinate system in the imaging region is created; a first two-dimensional matrix of defect images is defined according to the plurality of grid areas based on the three-dimensional orthogonal coordinate system; and a second two-dimensional matrix of magnetic flux leakage signals is created according to the magnetic flux leakage testing data based on the three-dimensional orthogonal coordinate system.

In some exemplary embodiments, the three-dimensional orthogonal coordinate system is created in the imaging region, and then the first two-dimensional matrix is defined, and the second two-dimensional matrix is created according to the magnetic flux leakage testing data. The first two-dimensional matrix and the second two-dimensional matrix are both based on the three-dimensional orthogonal coordinate system, and elements in the first two-dimensional matrix correspond respectively to elements in the second two-dimensional matrix.

In some embodiments, assuming that, x represents a coordinate corresponding to a defect length of the corrosion defect in the three-dimensional orthogonal coordinate system, Y represents a coordinate corresponding to a defect width of the corrosion defect in the three-dimensional orthogonal coordinate system, f(x,y) represents a defect depth of the corrosion defect, i.e. each pair of x and Y corresponds to a determined f(x,y). According to the above-described, M points are collected in the length direction of the corrosion defect and N points are collected in the width direction of the corrosion defect, so an image having M rows and N columns may be obtained and accordingly the first two-dimensional matrix may be obtained, in which the two-dimensional matrix is denoted by $$f(x,y) = \begin{bmatrix} f(0,0) & f(0,1) & \ldots & f(0, N-1) \\ f(1,0) & f(1,1) & \ldots & f(1, N-1) \\ \vdots & \vdots & & \vdots \\ f(M-1,0) & f(M-1,1) & \ldots & f(M-1, N-1) \end{bmatrix}.$$

In some embodiments, each element in the first two-dimensional matrix represents a defect depth at a pixel. In other words, each element in the first two-dimensional matrix corresponds to one pixel in S102, and a value of the element represents the defect depth.

In some embodiments, the magnetic flux leakage testing data includes magnetic flux leakage testing data in the axial direction of the pipeline to be tested, magnetic flux leakage testing data in the radial direction of the pipeline to be tested and magnetic flux leakage testing data in the circumferential direction of the pipeline to be tested. The second two-dimensional matrix, for example, includes a third two-dimensional matrix of magnetic flux leakage signals in the axial direction of the pipeline to be tested, a fourth two-dimensional matrix of magnetic flux leakage signals in the radial direction of the pipeline to be tested and a fifth two-dimensional matrix of magnetic flux leakage signals in the circumferential direction of the pipeline to be tested.

In some embodiments, the third two-dimensional matrix is denoted respectively by $$B_a = \begin{bmatrix} B_{a11} & B_{a12} & \ldots & B_{a1K} \\ B_{a21} & B_{a22} & \ldots & B_{a2K} \\ \vdots & \vdots & \vdots & \vdots \\ B_{aJ1} & B_{aJ2} & \ldots & B_{aJK} \end{bmatrix}$$

the fourth two-dimensional matrix is denoted by $$B_r = \begin{bmatrix} B_{r11} & B_{r12} & \ldots & B_{r1K} \\ B_{r21} & B_{r22} & \ldots & B_{r2K} \\ \vdots & \vdots & \vdots & \vdots \\ B_{rJ1} & B_{rJ2} & \ldots & B_{rJK} \end{bmatrix}$$

the fifth two-dimensional matrix is denoted by $$B_c = \begin{bmatrix} B_{c11} & B_{c12} & \ldots & B_{c1K} \\ B_{c21} & B_{c22} & \ldots & B_{c2K} \\ \vdots & \vdots & \vdots & \vdots \\ B_{cJ1} & B_{cJ2} & \ldots & B_{cJK} \end{bmatrix}$$

where J represents a number of measuring points in a axial direction of the pipeline to be tested, K represents a number of measuring points in a circumferential direction of the pipeline to be tested, $B_{a11}$ represents a magnetic flux leakage signal in the axial direction at a measuring point representing a first measuring point in the axial direction and a first measuring point in the circumferential direction; $B_{aJK}$ represents a magnetic flux leakage signal in the axial direction at a measuring point representing a $J^{th}$ measuring point in the axial direction and a $K^{th}$ measuring point in the circumferential direction; $B_{r11}$ represents a magnetic flux leakage signal in the radial direction at a measuring point representing a first measuring point in the axial direction and a first measuring point in the circumferential direction; $B_{rJK}$ represents a magnetic flux leakage signal in the radial direction at a measuring point representing a $J^{th}$ measuring point in the axial direction and a $K^{th}$ measuring point in the circumferential direction; $B_{c11}$ represents a magnetic flux leakage signal in the circumferential direction at a measuring point representing a first measuring point in the axial direction and a first measuring point in the circumferential direction; $B_{cJK}$ represents a magnetic flux leakage signal in the circumferential direction at a measuring point representing a $J^{th}$ measuring point in the axial direction and a $K^{th}$ measuring point in the circumferential direction.

In some embodiments, J is equal to M, and K is equal to N.

The defect length is estimated through the magnetic flux leakage signals in the radial direction, the defect width is estimated through the magnetic flux leakage signals in the circumferential direction and the defect depth is estimated through the magnetic flux leakage signals in the axial direction and the magnetic flux leakage signals in the radial direction.

In step 105, the second two-dimensional matrix is mapped to the first two-dimensional matrix using a pre-trained wavelet neural network so as to image the corrosion defect.

Figure 3:
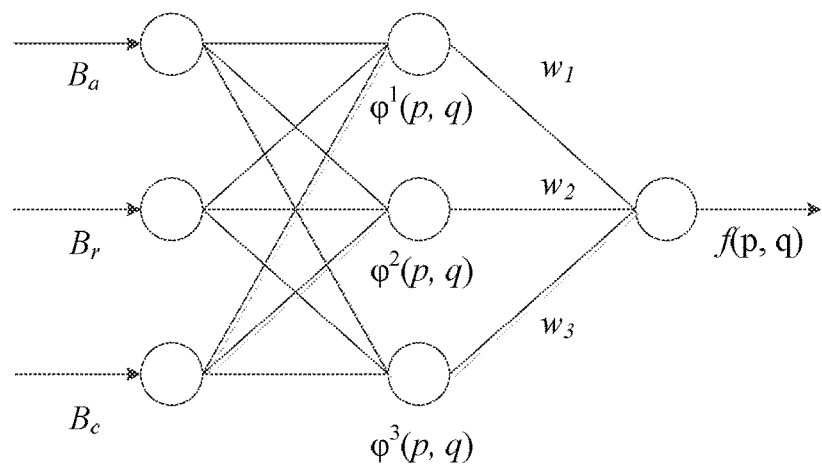
FIG. 3 is a schematic diagram illustrating a wavelet neural network in an imaging method based on a magnetic flux leakage testing according to an embodiment of the present disclosure.

In some exemplary embodiments, combining FIG. 3, there are three hidden layers, an output $q(p) \in L^2(R)$ of the pre-trained wavelet neural network is denoted by $$q(p) = \sum_{i=1}^{3} w_i \varphi^i [D_i R_i (p - t_i)] + \bar{q},$$

$$\varphi^i(p) = Q^{i1}(p_1)\varphi^{i1}(p_2) \ldots \varphi^{i1}(p_n), i = 1, 2, 3,$$

$$\forall\, p = (p_1, p_2, \ldots, p_n) \in R^n,$$

$$t_i \in R^n, D_i = \mathrm{diag}(d_i), d_i \in R_+^n, w_i \in R^n,$$

where p represents an input of the pre-trained wavelet neural network, which is a matrix, $p_n$ represents a row vector of p, n represents a number of rows in p, q represents the output of the pre-trained wavelet neural network, $w_i$ represents a connection weight, $\varphi^i(p)$ represents a multi-dimensional wavelet function corresponding to the $i^{th}$ the hidden layer and composed of $\varphi^{i1}$, $\varphi^{i1}$ represents a one-dimensional wavelet function corresponding to the $i^{th}$ the hidden layer, $t_i$ represents a translation vector, $D_i$ represents an expansion vector, $R_i$ a rotation matrix, $\bar{q}$ represents an average value of an approximation function. It may be seen from the above formula that, a mapping of $R^n \rightarrow R$ is realized by a mapping of $p \rightarrow q(p)$.

Further, three groups (count up to 48) of testing data of different defects may be selected to train the pre-trained wavelet neural network. The first group includes 16 variable-length defects, in which the width of each of the 16 variable-length defects is 2.5T, the depth of each of the 16 variable-length defects is 0.25T, and the lengths of the 16 variable-length defects are from an array of 0.5T, 1T, . . . , 8T, difference between each two adjacent element in the array is 0.5T; the second group includes 16 variable-width defects, in which the length of each of the 16 variable-length defects is 2.5T, the depth of each of the 16 variable-length defects is 0.25T, and the widths of the 16 variable-length defects are from an array of 0.5T, 1T, . . . , 8T, difference between each two adjacent element in the array is 0.5T; the length of each of the 16 variable-length defects is 2.5T, the width of each of the 16 variable-length defects is 0.25T, and the depths of the 16 variable-length defects are from an array of 0.5T, 1T, . . . , 8T, difference between each two adjacent element in the array is 0.5T. A selected wavelet function may be the Mexican hat function, and a target error when the network is convergent may be $10^{-5}$, and a gradient descent method may be used to train the pre-trained wavelet neural network.

An imaging experiment for the defects is performed using the trained wavelet neural network. The magnetic flux leakage testing data obtained in step S103 may be used as experiment samples. Inputs of the trained wavelet neural network are the third two-dimensional matrix $B_a$, the fourth two-dimensional matrix $B_r$ and the fifth two-dimensional matrix $B_c$, in which the number of nodes input in the trained wavelet neural network is J×K; an output of the trained wavelet network is the first two-dimensional matrix f(x,y), in which the number of nodes output in from the trained wavelet neural network is M×N. Since the wavelet neural network has advantages of a nonlinear mapping, a precision approach and a rapid convergence, the third two-dimensional matrix $B_a$, the fourth two-dimensional matrix $B_r$ and the fifth two-dimensional matrix $B_c$ may be mapped to the first two-dimensional matrix f(x,y), such that the defect is imaged in three dimension.

In order to understand easily, with reference to FIGS. 2 and 3, the imaging method based on a magnetic flux leakage testing according to the above-described embodiments of the present disclosure will be described in detail using a specific example. In this specific example, with reference to FIGS. 2 and 3, the method includes following steps.

In step 10, the pipeline to be tested having the thickness 12 mm is selected, and the region having the area 40 mm×30 mm is selected from the pipeline as the imaging region, and the standard artificial corrosion defect having the length 32 mm, the width 20 mm and the depth 8 mm is formed in the imaging region. Then the imaging region is divided into 200×150 grid areas (i.e. 200×150 pixels), i.e. the defect length is discretized into 200 points and the defect width is discretized into 150 points, such that the sampling interval in the length direction of the imaging region is equal to S1=40/200=0.2 mm, the sampling interval in the width direction of the imaging region is equal to S2=30/150=0.2 mm, and the area occupied by each pixel is equal to 0.2×0.2=0.04 mm². Boundaries of the corrosion defect are transited naturally in arc.

In step 20, the saturation magnetization is performed on the wall of the pipeline by the direct current magnetic field, and the three-dimensional sensors samples data at equal intervals in the pipeline at the certain operating speed 0.25 m/s to obtain the magnetic flux leakage testing data in the axial direction, the magnetic flux leakage testing data in the radial direction and the magnetic flux leakage testing data in the circumferential direction, in which the liftoff value of the sensor is 2.0 mm, the sampling interval in the axial direction and the sampling interval in the radial direction both are 0.2 mm.

In step 30, all of the magnetic flux leakage testing data obtained in step 20 are calculated to obtain the average value, and 1.2 times of the average value is used as the anomaly threshold to exclude some obvious erroneous data and abnormal data.

In step 40, the three-dimensional orthogonal coordinate system of the imaging region is created in the imaging region; and then the first two-dimensional matrix f(x,y) of defect images is defined, in which x represents a coordinate corresponding to the defect length of the corrosion defect in the three-dimensional orthogonal coordinate system, y represents a coordinate corresponding to the defect width of the corrosion defect in the three-dimensional orthogonal coordinate system, f(x,y) represents the defect depth of the corrosion defect, i.e. each pair of x and Y corresponds to the determined f(x,y). According to the above-described, 200 points are collected in the length direction of the corrosion defect and 150 points are collected in the width direction of the corrosion defect, so the image having 200 rows and 150 columns may be obtained and accordingly the first two-dimensional matrix is denoted by $$f(x,y) = \begin{bmatrix} f(0,0) & f(0,1) & \cdots & f(0,149) \\ f(1,0) & f(1,1) & \cdots & f(1,149) \\ \vdots & \vdots & & \vdots \\ f(199,0) & f(199,1) & \cdots & f(199,149) \end{bmatrix},$$

Each element in the first two-dimensional matrix corresponds to one pixel in step 10, and a value of the element represents the defect depth.

In step 50, the second two-dimensional matrix of magnetic flux leakage signals is determined. Specially, the magnetic flux leakage testing data includes magnetic flux leakage testing data in the axial direction of the pipeline to be tested, magnetic flux leakage testing data in the radial direction of the pipeline to be tested and magnetic flux leakage testing data in the circumferential direction of the pipeline to be tested. The defect length is estimated through the magnetic flux leakage signals in the radial direction, the defect width is estimated through the magnetic flux leakage signals in the circumferential direction and the defect depth is estimated through the magnetic flux leakage signals in the axial direction and the magnetic flux leakage signals in the radial direction. The number of measuring points in the length direction of the corrosion defect is 200 and the number of measuring points in the width direction of the corrosion defect is 150, and the three corresponding two-dimensional matrixes of magnetic flux leakage signals are denoted respectively by $$B_a = \begin{bmatrix} B_{a11} & B_{a12} & \cdots & B_{a1K} \\ B_{a21} & B_{a22} & \cdots & B_{a2K} \\ \vdots & \vdots & \vdots & \vdots \\ B_{aJ1} & B_{aJ2} & \cdots & B_{aJK} \end{bmatrix},$$

$$B_r = \begin{bmatrix} B_{r11} & B_{r12} & \cdots & B_{r1K} \\ B_{r21} & B_{r22} & \cdots & B_{r2K} \\ \vdots & \vdots & \vdots & \vdots \\ B_{rJ1} & B_{rJ2} & \cdots & B_{rJK} \end{bmatrix},$$

$$B_c = \begin{bmatrix} B_{c11} & B_{c12} & \cdots & B_{c1K} \\ B_{c21} & B_{c22} & \cdots & B_{c2K} \\ \vdots & \vdots & \vdots & \vdots \\ B_{cJ1} & B_{cJ2} & \cdots & B_{cJK} \end{bmatrix},$$

In step 60, the second two-dimensional matrix is mapped to the first two-dimensional matrix using a wavelet neural network. Specially, combing FIG. 3, there are three hidden layers, the output $q(p) \in L^2(R)$ of the wavelet neural network is denoted by $$q(p) = \sum_{i=1}^{3} w_i \varphi^i [D_i R_i (p - t_i)] + \bar{q},$$

$$\varphi^i(p) = \varphi^{i1}(p_1) \varphi^{i1}(p_2) \cdots \varphi^{i1}(p_n), i = 1, 2, 3,$$

$$\forall\, p = (p_1, p_2, \ldots, p_n) \in R^n,$$

$$t_i \in R^n, D_i = \mathrm{diag}(d_i), d_i \in R_+^n, w_i \in R^n,$$

where p represents an input of the wavelet neural network, which is a matrix, $p_n$ represents a row vector of p, n represents a number of rows in p, q represents the output of the wavelet neural network, $w_i$ represents a connection weight, $\varphi^i(p)$ represents a multi-dimensional wavelet function corresponding to the $i^{th}$ the hidden layer and composed of $\varphi^{i1}$, $\varphi^{i1}$ represents a one-dimensional wavelet function corresponding to the $i^{th}$ the hidden layer, $t_i$ represents a translation vector, $D_i$ represents an expansion vector, $R_i$ a rotation matrix, $\bar{q}$ represents an average value of an approximation function. It may be seen from the above formula that, a mapping of $R^n \rightarrow R$ is realized by a mapping of $p \rightarrow q(p)$.

Then, three groups (count up to 48) of testing data of different defects may be selected to train the wavelet neural network. The first group includes 16 variable-length defects, in which the width of each of the 16 variable-length defects is 30 mm, the depth of each of the 16 variable-length defects is 3 mm, the lengths of the 16 variable-length defects are from an array of 6 mm, 12 mm, . . . , 96 mm, difference between each two adjacent element in the array is 6 mm; the second group includes 16 variable-width defects, in which the length of each of the 16 variable-length defects is 30 mm, the depth of each of the 16 variable-length defects is 3 mm, the widths of the 16 variable-length defects are from an array of 6 mm, 12 mm, . . . , 96 mm, difference between each two adjacent element in the array is 6 mm; the third group includes 16 variable-depth defects, in which the length of each of the 16 variable-length defects is 30 mm, the width of each of the 16 variable-length defects is 30 mm, the depths of each of the 16 variable-length defects is 0.6 mm, 1.2 mm, . . . , 9.6 mm, difference between each two adjacent element in the array is 6 mm. The selected wavelet function may be the Mexican hat function, and the target error when the wavelet neural network is convergent may be $10^{-5}$, and the wavelet neural network is convergent after 1182 iterations.

The imaging experiment for the defects is performed using the trained wavelet neural network. The magnetic flux leakage testing data obtained in step 30 may be used as experiment samples. Inputs of the wavelet neural network are the two-dimensional matrixes of magnetic flux leakage signals $B_a$, $B_r$ and $B_c$, in which the number of nodes input in the trained wavelet neural network is 200×150=30000; an output of the number of nodes output in from the trained wavelet neural network is network is the two-dimensional first matrix f(x,y) of defect images, in which the number of nodes output in from the trained wavelet neural network is 200×150=30000. Since the wavelet neural network has advantages of the nonlinear mapping, the precision approach, and the rapid convergence, the two-dimensional matrixes of magnetic flux leakage signals $B_a$, $B_r$ and $B_c$ may be mapped to the first two-dimensional matrix f(x,y) of defect images, such that the defect is imaged in three dimension. Further, according to the testing data, the defect having the length 30.2 mm, the width 21.5 mm and the depth 7.4 mm is calculated, in which the boundaries of the defect are transited naturally in arc and the calculated defect has a good agreement with the actual defect, thus obtaining a high imaging accuracy.

In summary, with the imaging method based on a magnetic flux leakage testing according to embodiments of the present disclosure, the imaging region of the defect is discretized, i.e. the imaging region is divided into the plurality of grid areas, in which each grid area represents a pixel, then the pipeline to be tested is scanned by the three-dimensional sensor array to obtain the magnetic flux leakage testing data, and then the three-dimensional orthogonal coordinate system is created in the imaging region while the first two-dimensional matrix of defect images and the second two-dimensional matrix of magnetic flux leakage signals are defined, in which the elements of the first two-dimensional matrix correspond respectively to the elements of the second two-dimensional matrix, and finally the second two-dimensional matrix is mapped into the first two-dimensional matrix using the pre-trained wavelet neural network, such that a reconstruction of a three-dimensional contour of the defect is realized. Therefore, the method obtains the data by the three-dimensional sensor array and the signal characteristics are from many sources, thus overcoming a disadvantage of only using characteristics of magnetic flux leakage signals in the axial direction to estimate in the conventional technology, meanwhile, the method takes advantages of a parallel computing, a fast speed and a accurate mapping in the training of the wavelet neural network, thus realizing a three-dimensional imaging and visualization of the defect and having a broad application prospect.

In order to realize the above-described embodiments, the present disclosure also provides an imaging apparatus based on a magnetic flux leakage testing.

Figure 4:
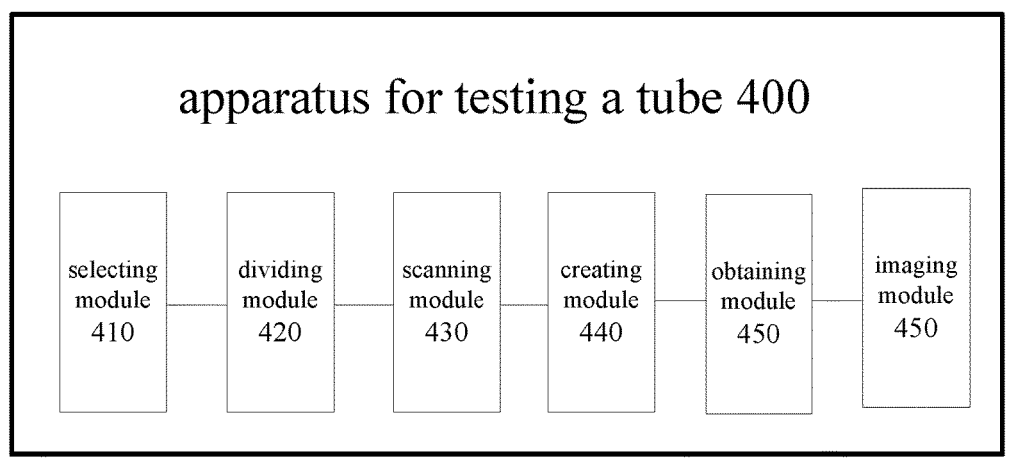
FIG. 4 is a block diagram illustrating an imaging apparatus based on a magnetic flux leakage testing according to an embodiment of the present disclosure.

FIG. 4 is a block diagram illustrating an imaging apparatus based on a magnetic flux leakage testing according to an embodiment of the present disclosure. As shown in FIG. 4, the imaging apparatus 400 includes a selecting module 410, a dividing module 420, a scanning module 430, a creating module 440, an obtaining module 450 and an imaging module 460.

Specifically, the selecting module 410 is configured to select an imaging region having a corrosion defect on a pipeline to be tested. The dividing module 420 is configured to divide the imaging region into a plurality of grid areas.

In some exemplary embodiments, for example, the pipeline to be tested having a thickness T is provided, and then a region having an area A×B is selected from the pipeline as the imaging region. A standard artificial corrosion defect having a length 2.5T, a width 1.5T and a depth 0.1~1T is formed in the imaging region. And then the imaging region is divided into M×N grid areas (i.e. M×N pixels), i.e. a defect length is discretized into M points and a defect width is discretized into N points, such that a sampling interval in a length direction of the imaging region is equal to S1=A/M, a sampling interval in a width direction of the imaging region is equal to S2=B/N and an area occupied by each pixel is equal to S1×S2. Boundaries of the corrosion defect are transited naturally in arc. The thickness T is about 7.0~36.0 mm.

The scanning module 430 is configured to scan by a three-dimensional sensor array the pipeline to be tested so as to obtain magnetic flux leakage testing data.

In some embodiments, the imaging apparatus further includes a saturation magnetization performing module (not shown in FIG. 4), in which the saturation magnetization performing module is configured to perform a saturation magnetization on the pipeline to be tested by a direct current magnetic field before scanning by the three dimensional sensor array the pipeline to be tested.

In some embodiments, the scanning module 430 includes a first obtaining unit, a calculating unit, a second obtaining unit and a deleting unit (not shown in FIG. 4).

The first obtaining unit is configured to obtain original magnetic flux leakage data by scanning the pipeline to be tested.

In some exemplary embodiments, in other words, a saturation magnetization is performed on the pipeline to be tested by the direct current magnetic field, and then the three-dimensional array samples data at equal intervals in the pipeline to be tested at a certain operating speed to obtain the original magnetic flux leakage data, in which the original magnetic flux leakage data includes original magnetic flux leakage data in an axial direction, original magnetic flux leakage data in a radial direction and original magnetic flux leakage data in a circumferential direction. During the scanning, a liftoff value of the sensor is required to be maintained in 1.0~5.0 mm. The sensor is a Hall sensor, and the liftoff value of the sensor is a distance from the Hall sensor to a surface of an inner wall of the pipeline. The sampling interval d is 0.1~8.0 mm, and the operating speed V is 0.1~5.0 m/s.

The calculating unit is configured to calculate an average value of the original magnetic flux leakage data.

In some exemplary embodiments, in other words, the original magnetic flux leakage data obtained by the first obtaining unit is calculated to obtain the average value.

The second obtaining unit is configured to obtain an anomaly threshold according to the average value.

In some exemplary embodiments, the anomaly threshold is equal to 1.2~1.5 times of the average value.

The deleting unit is configured to filter the original magnetic flux leakage data according to the anomaly threshold to obtain the magnetic flux leakage testing data. In other words, the data in the original magnetic flux leakage data which is larger than the anomaly threshold obtained in step 3 is deleted, thus excluding some obvious erroneous data and abnormal data.

The creating module 440 is configured to create a three-dimensional orthogonal coordinate system in the imaging region, define a first two-dimensional matrix of defect images according to the plurality of grid areas based on the three-dimensional orthogonal coordinate system, and create a second two-dimensional matrix of magnetic flux leakage signals according to the magnetic flux leakage testing data based on the three-dimensional orthogonal coordinate system.

In some exemplary embodiments, the three-dimensional orthogonal coordinate system is created in the imaging region, and then the first two-dimensional matrix is defined, and the second two-dimensional matrix is created according to the magnetic flux leakage testing data. The first two-dimensional matrix and the second two-dimensional matrix are both based on the three-dimensional orthogonal coordinate system, and elements in the first two-dimensional matrix correspond respectively to elements in the second two-dimensional matrix In some embodiments, assuming that, x represents a coordinate corresponding to a defect length of the corrosion defect in the three-dimensional orthogonal coordinate system, y represents a coordinate corresponding to a defect width of the corrosion defect in the three-dimensional orthogonal coordinate system, f(x,y) represents a defect depth of the corrosion defect, i.e. each pair of x and Y corresponds to a determined f(x,y). According to the above-described, M points are collected in the length direction of the corrosion defect and N points are collected in the width direction of the corrosion defect, so an image having M rows and N columns may be obtained and accordingly the first two-dimensional matrix may be obtained, in which the two-dimensional matrix is denoted by $$f(x,y) = \begin{bmatrix} f(0,0) & f(0,1) & \ldots & f(0,N-1) \\ f(1,0) & f(1,1) & \ldots & f(1,N-1) \\ \vdots & \vdots & \vdots & \vdots \\ f(M-1,0) & f(M-1,1) & \ldots & f(M-1,N-1) \end{bmatrix}.$$

In some embodiments, each element in first the two-dimensional matrix of defect images represents a defect depth at a pixel. In other words, each element in the first matrix corresponds to one pixel, and a value of the element represents the defect depth.

In some embodiments, the magnetic flux leakage testing data includes magnetic flux leakage testing data in the axial direction of the pipeline to be tested, magnetic flux leakage testing data in the radial direction of the pipeline to be tested and magnetic flux leakage testing data in the circumferential direction of the pipeline to be tested. The second two-dimensional matrix, for example, includes a third two-dimensional matrix of magnetic flux leakage signals in the axial direction of the pipeline to be tested, a fourth two-dimensional matrix of magnetic flux leakage signals in the radial direction of the pipeline to be tested and a fifth two-dimensional matrix of magnetic flux leakage signals in the circumferential direction of the pipeline to be tested.

In some embodiments, the third two-dimensional matrix is denoted respectively by $$B_a = \begin{bmatrix} B_{a11} & B_{a12} & \ldots & B_{a1K} \\ B_{a21} & B_{a22} & \ldots & B_{a2K} \\ \vdots & \vdots & \vdots & \vdots \\ B_{aJ1} & B_{aJ2} & \ldots & B_{aJK} \end{bmatrix}$$

the fourth two-dimensional matrix is denoted by $$B_r = \begin{bmatrix} B_{r11} & B_{r12} & \ldots & B_{r1K} \\ B_{r21} & B_{r22} & \ldots & B_{r2K} \\ \vdots & \vdots & \vdots & \vdots \\ B_{rJ1} & B_{rJ2} & \ldots & B_{rJK} \end{bmatrix}$$

the fifth two-dimensional matrix is denoted by $$B_c = \begin{bmatrix} B_{c11} & B_{c12} & \ldots & B_{c1K} \\ B_{c21} & B_{c22} & \ldots & B_{c2K} \\ \vdots & \vdots & \vdots & \vdots \\ B_{cJ1} & B_{cJ2} & \ldots & B_{cJK} \end{bmatrix}$$

where J represents a number of measuring points in a axial direction of the pipeline to be tested, K represents a number of measuring points in a circumferential direction of the pipeline to be tested, $B_{a11}$ represents a magnetic flux leakage signal in the axial direction at a measuring point representing a first measuring point in the axial direction and a first measuring point in the circumferential direction; $B_{aJK}$ represents a magnetic flux leakage signal in the axial direction at a measuring point representing a $J^{th}$ measuring point in the axial direction and a $K^{th}$ measuring point in the circumferential direction; $B_{r11}$ represents a magnetic flux leakage signal in the radial direction at a measuring point representing a first measuring point in the axial direction and a first measuring point in the circumferential direction; $B_{rJK}$ represents a magnetic flux leakage signal in the radial direction at a measuring point representing a $J^{th}$ measuring point in the axial direction and a $K^{th}$ measuring point in the circumferential direction; $B_{c11}$ represents a magnetic flux leakage signal in the circumferential direction at a measuring point representing a first measuring point in the axial direction and a first measuring point in the circumferential direction; $B_{cJK}$ represents a magnetic flux leakage signal in the circumferential direction at a measuring point representing a $J^{th}$ measuring point in the axial direction and a $K^{th}$ measuring point in the circumferential direction.

In some embodiments, J is equal to M, and K is equal to N.

The defect length is estimated through the magnetic flux leakage signals in the radial direction, the defect width is estimated through the magnetic flux leakage signals in the circumferential direction and the defect depth is estimated through the magnetic flux leakage signals in the axial direction and the magnetic flux leakage signals in the radial direction.

The obtaining module 450 is configured to map the second two-dimensional matrix to the first two-dimensional matrix using a pre-trained wavelet neural network so as to image the corrosion defect.

In some exemplary embodiments, combining FIG. 3, there are three hidden layers, an output $q(p) \in L^2(R)$ of the pre-trained wavelet neural network is denoted by $$q(p) = \sum_{i=1}^{3} w_i \varphi^i [D_i R_i (p - t_i)] + \bar{q},$$

$$\varphi^i(p) = \varphi^{i1}(p_1) \varphi^{i1}(p_2) \ldots \varphi^{i1}(p_n), i = 1, 2, 3,$$

$$\forall\, p = (p_1, p_2, \ldots, p_n) \in R^n,$$

$$t_i \in R^n, D_i = \text{diag}(d_i), d_i \in R^n_+, w_i \in R^n,$$

where p represents an input of the pre-trained wavelet neural network, which is a matrix, $p_n$ represents a row vector of p, n represents a number of rows in p, q represents the output of the pre-trained wavelet neural network, $w_i$ represents a connection weight, $\varphi^i(p)$ represents a multi-dimensional wavelet function corresponding to the $i^{th}$ the hidden layer and composed of $\varphi^{i1}$, $\varphi^{i1}$ represents a one-dimensional wavelet function corresponding to the $i^{th}$ the hidden layer, $t_i$ represents a translation vector, $D_i$ represents an expansion vector, $R_i$ represents a rotation matrix, q represents an average value of an approximation function. It may be seen from the above formula that, a mapping of $R^n \to R$ is realized by a mapping of $p \to q(P)$.

Further, three groups (count up to 48) of testing data of different defects may be selected to train the pre-trained wavelet neural network. The first group includes 16 variable-length defects, in which the width of each of the 16 variable-length defects is 2.5T, the depth of each of the 16 variable-length defects is 0.25T, and the lengths of the 16 variable-length defects are from an array of 0.5T, 1T, . . . , 8T, difference between each two adjacent element in the array is 0.5T; the second group includes 16 variable-width defects, in which the length of each of the 16 variable-length defects is 2.5T, the depth of each of the 16 variable-length defects is 0.25T, and the widths of the 16 variable-length defects are from an array of 0.5T, 1T, . . . , 8T, difference between each two adjacent element in the array is 0.5T; the length of each of the 16 variable-length defects is 2.5T, the width of each of the 16 variable-length defects is 0.25T, and the depths of the 16 variable-length defects are from an array of 0.5T, 1T, . . . , 8T, difference between each two adjacent element in the array is 0.5T. A selected wavelet function may be the Mexican hat function, and a target error when the network is convergent may be $10^{-5}$, and a gradient descent method may be used to train the pre-trained wavelet neural network.

An imaging experiment for the defects is performed by the trained wavelet neural network. The magnetic flux leakage testing data obtained by the scanning module 430 may be used as experiment samples.

Inputs of the trained wavelet neural network are the third two-dimensional matrix $B_a$, the fourth two-dimensional matrix $B_r$ and the fifth two-dimensional matrix $B_c$, in which the number of nodes input in the trained wavelet neural network is J×K; an output of the trained wavelet network is the first two-dimensional matrix f(x,y), in which the number of nodes output in from the trained wavelet neural network is M×N. Since the wavelet neural network has advantages of a nonlinear mapping, a precision approach and a rapid convergence, the third two-dimensional matrix $B_a$, the fourth two-dimensional matrix $B_r$ and the fifth two-dimensional matrix $B_c$ may be mapped to the first two-dimensional matrix f(x,y), such that the defect is imaged in three dimension.

With respect to the devices in the above embodiments, the specific manners for performing operations for individual modules therein have been described in detail in the embodiments regarding the methods, which are not elaborated herein again.

In summary, with the imaging apparatus based on a magnetic flux leakage testing according to embodiments of the present disclosure, the imaging region of the defect is discretized, i.e. the imaging region is divided into the plurality of grid areas, in which each grid area represents a pixel, then the pipeline to be tested is scanned by the three-dimensional sensor array to obtain the magnetic flux leakage testing data, and then the three-dimensional orthogonal coordinate system is created in the imaging region while the first two-dimensional matrix of defect images and the second two-dimensional matrix of magnetic flux leakage signals are defined, in which the elements of the first two-dimensional matrix correspond respectively to the elements of the second two-dimensional matrix, and finally the second two-dimensional matrix is mapped into the first two-dimensional matrix using the pre-trained wavelet neural network, such that a reconstruction of a three-dimensional contour of the defect is realized. Therefore, the method obtains the data by the three-dimensional sensor array and the signal characteristics are from many sources, thus overcoming a disadvantage of only using characteristics of magnetic flux leakage signals in the axial direction to estimate in the conventional technology, meanwhile, the method takes advantages of a parallel computing, a fast speed and a accurate mapping in the training of the wavelet neural network, thus realizing a three-dimensional imaging and visualization of the defect and having a broad application prospect.

In the specification, unless specified or limited otherwise, relative terms such as "central", "longitudinal", "lateral", "front", "rear", "right", "left", "inner", "outer", "lower", "upper", "horizontal", "vertical", "above", "below", "up", "top", "bottom" as well as derivative thereof (e.g., "horizontally", "downwardly", "upwardly", etc.) should be construed to refer to the orientation as then described or as shown in the drawings under discussion. These relative terms are for convenience of description and do not require that the present disclosure be constructed or operated in a particular orientation.

In addition, terms such as "first" and "second" are used herein for purposes of description and are not intended to indicate or imply relative importance or significance. Thus, the feature defined with "first" and "second" may comprise one or more this feature. In the description of the present disclosure, "a plurality of" means at least two, for example, two or three, unless specified otherwise.

In the description of the present disclosure, it should be understood that, unless specified or limited otherwise, the terms "mounted," "connected," and "coupled" and variations thereof are used broadly and encompass such as mechanical or electrical mountings, connections and couplings, also can be inner mountings, connections and couplings of two components, and further can be direct and indirect mountings, connections, and couplings, which can be understood by those skilled in the art according to the detail embodiment of the present disclosure.

In the description, unless specified or limited otherwise, it is to be understood that phraseology and terminology used herein with reference to device or element orientation (for example, terms like "upper", "lower", and the like) should be construed to refer to the orientation as then described or as shown in the drawings under discussion for simplifying the description of the present disclosure, but do not alone indicate or imply that the device or element referred to must have a particular orientation. Moreover, it is not required that the present disclosure is constructed or operated in a particular orientation.

Reference throughout this specification to "an embodiment," "some embodiments," "one embodiment", "another example," "an example," "a specific example," or "some examples," means that a particular feature, structure, material, or characteristic described in connection with the embodiment or example is included in at least one embodiment or example of the present disclosure. Thus, the appearances of the phrases such as "in some embodiments," "in one embodiment", "in an embodiment", "in another example," "in an example," "in a specific example," or "in some examples," in various places throughout this specification are not necessarily referring to the same embodiment or example of the present disclosure. Furthermore, the particular features, structures, materials, or characteristics may be combined in any suitable manner in one or more embodiments or examples.

Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure.

What is claimed is:

1. An imaging method based on a magnetic flux leakage testing, comprising:
    selecting an imaging region having a corrosion defect on a pipeline to be tested;
    dividing the imaging region into a plurality of grid areas;
    scanning by a three-dimensional sensor array the pipeline to be tested so as to obtain magnetic flux leakage testing data;
    creating a three-dimensional orthogonal coordinate system in the imaging region, defining a first two-dimensional matrix of defect images according to the plurality of grid areas based on the three-dimensional orthogonal coordinate system, and creating a second two-dimensional matrix of magnetic flux leakage signals according to the magnetic flux leakage testing data based on the three-dimensional orthogonal coordinate system; and
    mapping the second two-dimensional matrix to the first two-dimensional matrix using a pre-trained wavelet neural network so as to image the corrosion defect.

2. The imaging method according to claim 1, wherein each grid area represents a pixel of the defect image and each element in the first two-dimensional matrix represents a defect depth at a pixel.

3. The imaging method according to claim 1, before scanning by a three dimensional sensor array the pipeline to be tested, further comprising:
    saturation magnetizing the pipeline to be tested by a direct current magnetic field.

4. The imaging method according to claim 1, wherein scanning by an three-dimensional sensor array the pipeline to be tested so as to obtain magnetic flux leakage testing data comprises:
    obtaining original magnetic flux leakage data by scanning the pipeline to be tested;
    calculating an average value of the original magnetic flux leakage data;
    obtaining an anomaly threshold according to the average value; and
    filtering the original magnetic flux leakage data according to the anomaly threshold to obtain the magnetic flux leakage testing data.

5. The imaging method according to claim 1, wherein the first two-dimensional matrix is denoted by $$f(x, y) = \begin{bmatrix} f(0, 0) & f(0, 1) & \ldots & f(0, N-1) \\ f(1, 0) & f(1, 1) & \ldots & f(1, N-1) \\ \vdots & \vdots & & \vdots \\ f(M-1, 0) & f(M-1, 1) & \ldots & f(M-1, N-1) \end{bmatrix}$$

where x represents a coordinate corresponding to a defect length of the corrosion defect in the three-dimensional orthogonal coordinate system, Y represents a coordinate corresponding to a defect width of the corrosion defect in the three-dimensional orthogonal coordinate system, M represents a number of pixels collected in a length direction of the corrosion defect, N represents a number of pixels collected in a width direction of the corrosion defect, f(x,y) represents a defect depth of the corrosion defect; f(0,0) represents a defect depth at a pixel representing a first pixel in the length direction and a first pixel in the width direction; f(0,1) represents a defect depth at a pixel representing a first pixel in the length direction and a second pixel in the width direction; f(M−1,N−1) represents a defect depth at a pixel representing a $M^{th}$ pixel in the length direction and a $N^{th}$ pixel in the width direction.

6. The imaging method according to claim 1, wherein the magnetic flux leakage testing data comprises: magnetic flux leakage testing data in an axial direction of the pipeline to be tested, magnetic flux leakage testing data in a radial direction of the pipeline to be tested and magnetic flux leakage testing data in a circumferential direction of the pipeline to be tested; and the second two-dimensional matrix comprises: a third two-dimensional matrix of magnetic flux leakage signals in the axial direction, a fourth two-dimensional matrix of magnetic flux leakage signals in the radial direction and a fifth two-dimensional matrix of magnetic flux leakage signals in the circumferential direction.

7. The imaging method according to claim 6, wherein the third two-dimensional matrix is denoted by $$B_a = \begin{bmatrix} B_{a11} & B_{a12} & \cdots & B_{a1K} \\ B_{a21} & B_{a22} & \cdots & B_{a2K} \\ \vdots & \vdots & \vdots & \vdots \\ B_{aJ1} & B_{aJ2} & \cdots & B_{aJK} \end{bmatrix};$$

the fourth two-dimensional matrix is denoted by $$B_r = \begin{bmatrix} B_{r11} & B_{r12} & \cdots & B_{r1K} \\ B_{r21} & B_{r22} & \cdots & B_{r2K} \\ \vdots & \vdots & \vdots & \vdots \\ B_{rJ1} & B_{rJ2} & \cdots & B_{rJK} \end{bmatrix};$$

the fifth two-dimensional matrix is denoted by $$B_c = \begin{bmatrix} B_{c11} & B_{c12} & \cdots & B_{c1K} \\ B_{c21} & B_{c22} & \cdots & B_{c2K} \\ \vdots & \vdots & \vdots & \vdots \\ B_{cJ1} & B_{cJ2} & \cdots & B_{cJK} \end{bmatrix},$$

where J represents a number of measuring points in the axial direction of the pipeline to be tested, K represents a number of measuring points in the circumferential direction of the pipeline to be tested, $B_{a11}$ represents a magnetic flux leakage signal in the axial direction at a measuring point representing a first measuring point in the axial direction and a first measuring point in the circumferential direction; $B_{aJK}$ represents a magnetic flux leakage signal in the axial direction at a measuring point representing a $J^{th}$ measuring point in the axial direction and a $K^{th}$ measuring point in the circumferential direction; $B_{r11}$ represents a magnetic flux leakage signal in the radial direction at a measuring point representing a first measuring point in the axial direction and a first measuring point in the circumferential direction; $B_{rJK}$ represents a magnetic flux leakage signal in the radial direction at a measuring point representing a $J^{th}$ measuring point in the axial direction and a $K^{th}$ measuring point in the circumferential direction; $B_{c11}$ represents a magnetic flux leakage signal in the circumferential direction at a measuring point representing a first measuring point in the axial direction and a first measuring point in the circumferential direction; $B_{cJK}$ represents a magnetic flux leakage signal in the circumferential direction at a measuring point representing a $j^{th}$ measuring point in the axial direction and a $K^{th}$ measuring point in the circumferential direction.

8. An imaging apparatus based on a magnetic flux leakage testing, comprising:
a processor;
a memory for storing instructions executable by the processor;
wherein the processor is configured to:
select an imaging region having a corrosion defect on a pipeline to be tested;
divide the imaging region into a plurality of grid areas;
control a three-dimensional sensor array to scan the pipeline to be tested to obtain magnetic flux leakage testing data;
create a three-dimensional orthogonal coordinate system in the imaging region, define a first two-dimensional matrix of defect images according to the plurality of grid areas based on the three-dimensional orthogonal coordinate system, and create a second two-dimensional matrix of magnetic flux leakage signals according to the magnetic flux leakage testing data based on the three-dimensional orthogonal coordinate system; and
map the second two-dimensional matrix to the first two-dimensional matrix using a pre-trained wavelet neural network so as to image the corrosion defect.

9. The imaging apparatus according to claim 8, wherein each grid area represents a pixel of the defect image and each element in the first two-dimensional matrix represents a defect depth at a pixel.

10. The imaging apparatus according to claim 8, wherein the processor further configured to:
saturation magnetize on the pipeline to be tested by a direct current magnetic field before controlling a three-dimensional sensor array to scan the pipeline to be tested.

11. The imaging apparatus according to claim 8, wherein the processor is configured to control a three-dimensional sensor array to scan the pipeline to be tested so as to obtain magnetic flux leakage testing data by steps of:
obtaining original magnetic flux leakage data by scanning the pipeline to be tested;
calculating an average value of the original magnetic flux leakage data;
obtaining an anomaly threshold according to the average value;
filtering the original magnetic flux leakage data according to the anomaly threshold to obtain the magnetic flux leakage testing data.

12. The imaging apparatus according to claim 8, wherein the first two-dimensional matrix is denoted by $$f(x, y) = \begin{bmatrix} f(0,0) & f(0,1) & \cdots & f(0, N-1) \\ f(1,0) & f(1,1) & \cdots & f(1, N-1) \\ \vdots & \vdots & & \vdots \\ f(M-1, 0) & f(M-1, 1) & \cdots & f(M-1, N-1) \end{bmatrix}$$

where x represents a coordinate corresponding to a defect length of the corrosion defect in the three-dimensional orthogonal coordinate system, Y represents a coordinate corresponding to a defect width of the corrosion defect in the three-dimensional orthogonal coordinate system, M represents a number of pixels collected in a length direction of the corrosion defect, N represents a number of pixels collected in a width direction of the corrosion defect, f(x,y) represents a defect depth of the corrosion defect; f(0,0) represents a defect depth at a pixel representing a first pixel in the length direction and a first pixel in the width direction; f(0,1) represents a defect depth at a pixel representing a first pixel in the length direction and a second pixel in the width direction; f(M−1,N−1) represents a defect depth at a pixel representing a $M^{th}$ pixel in the length direction and a $N^{th}$ pixel in the width direction.

13. The imaging apparatus according to claim 8, wherein the magnetic flux leakage testing data comprises: magnetic flux leakage testing data in an axial direction of the pipeline to be tested, magnetic flux leakage testing data in a radial direction of the pipeline to be tested and magnetic flux leakage testing data in a circumferential direction of the pipeline to be tested; and the second two-dimensional matrix comprises: a third two-dimensional matrix of magnetic flux leakage signals in the axial direction, a fourth two-dimensional matrix of magnetic flux leakage signals in the radial direction and a fifth two-dimensional matrix of magnetic flux leakage signals in the circumferential direction.

14. The imaging apparatus according to claim 13, wherein the third two-dimensional matrix is denoted by $$B_a = \begin{bmatrix} B_{a11} & B_{a12} & \cdots & B_{a1K} \\ B_{a21} & B_{a22} & \cdots & B_{a2K} \\ \vdots & \vdots & \vdots & \vdots \\ B_{aJ1} & B_{aJ2} & \cdots & B_{aJK} \end{bmatrix};$$

the fourth two-dimensional matrix is denoted by $$B_r = \begin{bmatrix} B_{r11} & B_{r12} & \cdots & B_{r1K} \\ B_{r21} & B_{r22} & \cdots & B_{r2K} \\ \vdots & \vdots & \vdots & \vdots \\ B_{rJ1} & B_{rJ2} & \cdots & B_{rJK} \end{bmatrix};$$

the fifth two-dimensional matrix is denoted by $$B_c = \begin{bmatrix} B_{c11} & B_{c12} & \cdots & B_{c1K} \\ B_{c21} & B_{c22} & \cdots & B_{c2K} \\ \vdots & \vdots & \vdots & \vdots \\ B_{cJ1} & B_{cJ2} & \cdots & B_{cJK} \end{bmatrix},$$

where J represents a number of measuring points in a axial direction of the pipeline to be tested, K represents a number of measuring points in a circumferential direction of the pipeline to be tested, $B_{a11}$ represents a magnetic flux leakage signal in the axial direction at a measuring point representing a first measuring point in the axial direction and a first measuring point in the circumferential direction; $B_{aJK}$ represents a magnetic flux leakage signal in the axial direction at a measuring point representing a $J^{th}$ measuring point in the axial direction and a $K^{th}$ measuring point in the circumferential direction; $B_{r11}$ represents a magnetic flux leakage signal in the radial direction at a measuring point representing a first measuring point in the axial direction and a first measuring point in the circumferential direction; $B_{rJK}$ represents a magnetic flux leakage signal in the radial direction at a measuring point representing a $J^{th}$ measuring point in the axial direction and a $K^{th}$ measuring point in the circumferential direction; $B_{c11}$ represents a magnetic flux leakage signal in the circumferential direction at a measuring point representing a first measuring point in the axial direction and a first measuring point in the circumferential direction; $B_{cJK}$ represents a magnetic flux leakage signal in the circumferential direction at a measuring point representing a $J^{th}$ measuring point in the axial direction and a $K^{th}$ measuring point in the circumferential direction.

15. A non-transitory computer readable storage medium having stored therein a computer program, when executed by a computer, to perform an imaging method based on a magnetic flux leakage testing, which comprises:
　selecting an imaging region having a corrosion defect on a pipeline to be tested;
　dividing the imaging region into a plurality of grid areas;
　scanning by a three-dimensional sensor array the pipeline to be tested so as to obtain magnetic flux leakage testing data;
　creating a three-dimensional orthogonal coordinate system in the imaging region, defining a first two-dimensional matrix of defect images according to the plurality of grid areas based on the three-dimensional orthogonal coordinate system, and creating a second two-dimensional matrix of magnetic flux leakage signals according to the magnetic flux leakage testing data based on the three-dimensional orthogonal coordinate system; and
　mapping the second two-dimensional matrix to the first two-dimensional matrix using a pre-trained wavelet neural network so as to image the corrosion defect.

* * * * *